United States Patent
Grunden et al.

(10) Patent No.: US 10,080,679 B2
(45) Date of Patent: Sep. 25, 2018

(54) THUMB ORTHOSIS

(71) Applicant: BSN medical GmbH, Hamburg (DE)

(72) Inventors: Jennifer Grunden, Hamburg (DE);
Timo Schmeltzpfenning, Buchholz (DE); Joachim Bauer, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 249 days.

(21) Appl. No.: 14/397,329

(22) PCT Filed: Apr. 26, 2013

(86) PCT No.: PCT/EP2013/058818
§ 371 (c)(1),
(2) Date: Feb. 3, 2015

(87) PCT Pub. No.: WO2013/160478
PCT Pub. Date: Oct. 31, 2013

(65) Prior Publication Data
US 2015/0157483 A1    Jun. 11, 2015

Related U.S. Application Data

(60) Provisional application No. 61/638,746, filed on Apr. 26, 2012.

(30) Foreign Application Priority Data

Apr. 26, 2012 (DE) .......................... 10 2012 008 565

(51) Int. Cl.
*A61F 5/00* (2006.01)
*A61F 5/01* (2006.01)

(52) U.S. Cl.
CPC ............ *A61F 5/013* (2013.01); *A61F 5/0118* (2013.01)

(58) Field of Classification Search
CPC ............ A61F 5/0118; A61F 2005/0186; A61F 5/05866; A61F 5/013; A61F 5/05875;
(Continued)

(56) References Cited

U.S. PATENT DOCUMENTS 3,124,127 A * 3/1964 Ruuska ............... A61F 5/05866
602/21
4,558,694 A * 12/1985 Barber ................ A61F 5/05866
602/21
(Continued)

FOREIGN PATENT DOCUMENTS

CH          684300 A5 *  8/1994  ....... A41D 19/01588
DE          3519493 A1   12/1986
(Continued)

OTHER PUBLICATIONS

International Search Report PCT/EP2013/058818 dated Jul. 2, 2013.

*Primary Examiner* — Kim M Lewis
(74) *Attorney, Agent, or Firm* — Shumaker, Loop & Kendrick, LLP

(57) ABSTRACT

An orthosis for fastening to a human hand for immobilizing the carpometacarpal joint and metacarpophalangeal joint of the thumb of the hand has a stiff body which can be of multi-piece or single-piece design. The rigidity of the body enables the latter to support, to stabilize and to immobilize the hand and dimensional stability is provided such that the body can be placed in a simple manner with a defined shape onto the hand.

17 Claims, 12 Drawing Sheets

(58) Field of Classification Search
CPC .... A61F 5/37; A61F 5/10; A61F 13/10; A61F 13/104; A61F 13/105; A61F 13/107; A61F 13/108; A41D 19/01588; A41D 13/08; A41D 13/081; A41D 13/082; A41D 13/087; A41D 13/088; A63B 71/14; A63B 71/143
USPC ........... 602/21, 22, 5, 6; 2/16, 21, 159, 161; 128/878, 879, 880
See application file for complete search history.

(56) References Cited

U.S. PATENT DOCUMENTS

| | | | | |
|---|---|---|---|---|
| 4,632,105 | A * | 12/1986 | Barlow | A61F 13/108 602/64 |
| 4,854,310 | A | 8/1989 | Lee | |
| 4,862,877 | A * | 9/1989 | Barber | A61F 5/05866 602/22 |
| 4,953,568 | A * | 9/1990 | Theisler | A61F 13/105 128/878 |
| 5,279,545 | A * | 1/1994 | Reese, Sr. | A61F 5/013 602/21 |
| 5,584,799 | A * | 12/1996 | Gray | A61F 5/05866 602/18 |
| 5,600,853 | A * | 2/1997 | Yewer, Jr. | A41D 13/082 2/161.1 |
| 5,746,707 | A * | 5/1998 | Eck | A61F 5/0118 128/878 |
| 5,771,901 | A * | 6/1998 | O'Brien | A41D 19/01523 128/878 |
| 5,787,896 | A * | 8/1998 | Sackett | A61F 5/0118 128/880 |
| 5,836,902 | A * | 11/1998 | Gray | A61F 5/0111 128/882 |
| 5,899,870 | A * | 5/1999 | Deirmendjian | A61F 5/0118 128/880 |
| 5,947,915 | A * | 9/1999 | Thibodo, Jr. | A61F 5/0118 602/22 |
| 6,146,347 | A * | 11/2000 | Porrata | A61F 5/0118 128/879 |
| 6,520,925 | B1 * | 2/2003 | Thibodo, Jr. | A61F 5/05875 128/880 |
| 6,849,056 | B1 * | 2/2005 | Wiggins | A61F 5/0118 128/879 |
| 7,179,180 | B1 * | 2/2007 | Frost | A63B 23/16 2/20 |
| 7,431,671 | B1 * | 10/2008 | Frost | A63B 69/0002 2/20 |
| D643,931 | S * | 8/2011 | Voskuilen | D24/190 |
| 2003/0125652 | A1 * | 7/2003 | Porrata | A61F 5/0118 602/21 |
| 2007/0028357 | A1 * | 2/2007 | Adams, Jr. | A63B 21/045 2/163 |
| 2007/0225629 | A1 * | 9/2007 | Israel | A61F 5/0118 602/21 |
| 2011/0208100 | A1 * | 8/2011 | Eck | A61F 5/0118 602/21 |
| 2013/0197411 | A1 * | 8/2013 | Bolla | A61F 5/05866 602/22 |
| 2013/0317789 | A1 * | 11/2013 | Summit | A61F 5/01 703/1 |
| 2014/0081188 | A1 * | 3/2014 | Hargis | A61F 5/05866 602/7 |

FOREIGN PATENT DOCUMENTS

| | | | |
|---|---|---|---|
| DE | 202009017438 U1 | 3/2010 | |
| EP | 0850573 A2 * | 7/1998 | ....... A41D 19/01588 |
| WO | 96/27349 A1 | 9/1996 | |
| WO | WO 0035390 A1 * | 6/2000 | ........... A41D 13/088 |
| WO | WO 2007066367 A2 * | 6/2007 | ........... A61F 5/0118 |
| WO | WO 2016011999 A1 * | 1/2016 | ........... A61F 5/0118 |

* cited by examiner

THUMB ORTHOSIS

TECHNICAL FIELD AND BACKGROUND OF THE INVENTION

The present invention relates to an orthosis for fastening to a human hand for immobilizing the carpometacarpal joint and metacarpophalangeal joint of the thumb of the hand.

Orthoses of this type are used in order to immobilize and fix the carpometacarpal joint and/or metacarpophalangeal joint of a user within the scope of treatment for chronic, posttraumatic or postoperative states of sensitivity or other pathological states in the region of said joints and to secure said joints in a defined position. One example of a pathological state in which such an orthosis can advantageously be used is what is referred to as rhizarthrosis of the thumb, i.e. arthrosis or degenerative chondrolysis in the region of the carpometacarpal joint. A further example is what is referred to as ski thumb in which, following the thumb being bent away outward in the metacarpophalangeal joint, for example in the event of a fall, an ulnar collateral ligament tear of the thumb has occurred.

It is desirable here for the functionality of the user's hand to be restricted as far as possible only insofar as is required for immobilizing or fixing the affected joints. In particular, it is desirable to put the user in the position of still being able to carry out a pinch grip by the thumb being secured in a position opposite the index finger, and the index finger being able to be brought into contact with the thumb in the manner of pincers in order to grasp objects.

Known orthoses are generally configured in such a manner that, when used correctly, said orthoses are adjacent to the wrist or end at the latter and therefore interfere with movements in the wrist and cause pressure points. Furthermore, they are generally configured in such a manner that they engage around the metacarpophalangeal joint of the thumb and provide an extensive covering of the thumb as far as the distal phalanx. One example is the orthosis which is disclosed in DE 20 2009 017 438 U1 and has a tubular main section and a thumb section. The main section is configured and dimensioned in such a manner that, when the orthosis is placed onto a hand, said main section at least partially surrounds the forearm and surrounds the carpal bone region and extends here from a forearm-side end facing the elbow joint over the wrist itself and the carpal bones as far as the metacarpal bones of the fingers. In order to accommodate the thumb, the thumb section extends from the main section to the side and is arranged and dimensioned in such a manner that, when put on, said thumb section surrounds the metacarpal bone of the thumb and extends at least along part of the proximal phalanx of the thumb beyond the metacarpophalangeal joint. Stabilizing bars are incorporated in the region of the thumb section, said stabilizing bars, when put on, extending laterally in the longitudinal direction of the thumb and being secured by the main section and the thumb section.

Orthoses of this design can indeed in principle provide a good immobilizing action. However, in practice, the immobilization actually achieved is insufficient. The lateral splinting for the thumb still permits a high degree of residual mobility. Nevertheless, the orthoses always restrict the mobility of the wrist. In addition, they frequently have large amounts of textile portions which are associated with the problems of rapid soiling and resultingly required cleaning, during which the patient cannot use the orthosis. By contrast, in the case of the known orthoses, the use of plastics conceals a high potential for pressure points. In addition, they are frequently difficult to put on, in particular taking into consideration the fact that the user has only one hand available.

SUMMARY OF THE INVENTION

It is the object of the present invention to provide a simply designed orthosis for fastening to a human hand for immobilizing the carpometacarpal joint and metacarpophalangeal joint of the thumb of the hand, by means of which orthosis a reliable fixing of the thumb in all directions of movement can be achieved and which nevertheless reduces the impairment to the mobility and functionality of the wrist in comparison to the prior art and overcomes the disadvantages mentioned.

This object is achieved by the orthosis disclosed herein. Advantageous embodiments of the orthosis are further provided.

According to the present invention, it is provided that an orthosis for fastening to a human hand for immobilizing the carpometacarpal joint and metacarpophalangeal joint of the thumb of the hand has a stiff body which, as will also be explained, can be of multi-piece or preferably single-piece design. It is also possible here for the orthosis as a whole to be formed by the stiff body or to consist of the stiff body.

The rigidity of the body enables the latter to support, to stabilize and to immobilize the hand in a desired manner, and dimensional stability is provided such that the body can be placed in a simple manner with a defined shape onto the hand. Despite the stiff design of the body, said body will generally have a certain degree of elasticity, making it easier to place it on.

Furthermore, it is preferred if the body is plastically deformable when a sufficient force is applied, possibly in conjunction with the action of heat, in order to permit simple adaptation to the hands of different users.

The stiff body firstly has a metacarpal section which is formed by a curved and stiff section of an element. This also comprises the possibility that the entire element forms the metacarpal section, and the possibility that the entire stiff body is formed by the element, or the stiff body is identical to the element. The element, the stiff body or at least the metacarpal section are preferably flat, band-shaped or two-dimensional. The metacarpal section has a first end and a second end which is spaced apart from the latter. The metacarpal section here can be elongate, wherein the first and the second end are then spaced apart from each other in the longitudinal direction.

The metacarpal section is furthermore designed in such a manner that it can be brought into engagement with a human hand by being placed against the palm of the hand below the metacarpophalangeal joints of an index finger, middle finger, ring finger and small finger and above the carpus such that it extends in the circumferential direction of the metacarpus at least partially over the palm and, in the process, rests completely or partially against the latter. In more precise terms, said metacarpal section extends in the circumferential direction of the metacarpus or in a direction between the two edges of the hand over the entire palm or at least part of the palm and rests completely or partially against the latter. For this purpose, the orthosis preferably has a contact surface which, in the case of a flat, band-shaped or two-dimensional configuration of the metacarpal section, is formed by an expanded side of the metacarpal section. In a preferred embodiment, the metacarpal section extends over the palm substantially perpendicularly to the longitudinal axis of the forearm in the anatomical normal position of hand and forearm. By means of this configuration of the metacarpal section, the latter, when placed on, is advantageously arranged in the region of the metacarpus and is at a distance from the wrist in the direction of the fingers. Therefore, the wrist is advantageously not covered and remains freely movable.

It can be provided here that the two ends of the metacarpal section are connected or can be connected by an elastic or flexible element or a plurality of elastic or flexible elements which, together with the metacarpal section and optionally further sections or elements of the orthosis, forms or form an annularly closed section which, when used in the described correct way, completely encircles the metacarpus of the user.

In addition, the stiff body has a stiff thumb section which, in a preferred embodiment, is likewise formed by a curved and stiff section of the element forming the metacarpal section. The thumb section constitutes an extension on the metacarpal section, the extension accommodating the thumb and extending from the metacarpal section and having a first end, which is fastened to the metacarpal section or is formed by part of the metacarpal section or is identical thereto, and having a second end. If the first end of the thumb section is formed by part of the metacarpal section or is identical thereto, the metacarpal section and the thumb section, and therefore the stiff body, are of single-piece design. Otherwise, the metacarpal section and the thumb section are provided as separate components which can be connected rigidly to each other. In the region of its second end, the thumb section has a ring-shaped or ring-segment-shaped thumb holding section.

Overall, the thumb section is designed in such a manner that, when the metacarpal section is brought into engagement in the above manner with the hand, said thumb section can be placed against the thumb of the hand such that the thumb extends through the ring-shaped or ring-segment-shaped thumb holding section, i.e. through the ring opening defined by the thumb holding section, and that the thumb holding section then extends over at least part of the circumference of the thumb and entirely or at least partially surrounds the latter and, in the process, supports the thumb against a movement in the direction of the palm, i.e. adduction, and against a movement in the opposite direction, i.e. abduction, and against flexion of the metacarpal joint. For this purpose, a concave surface of the ring-shaped or ring-segment-shaped thumb holding section, which surface is provided for contact with the thumb, is preferably arranged in such a manner that, when the orthosis is placed on a hand, said surface rests at least also against the palm-facing inner side of the thumb. However, it is also possible for such a concave surface provided for contact with the thumb at least also to rest on the opposite side of the thumb. The thumb holding section is supported in a position in which the thumb and the index finger of the hand are put opposite each other and the index finger can be moved toward the thumb into contact therewith and away from the thumb. In other words, the hand is immobilized or fixed in a functional position in which the user can carry out the important pinch grip.

In a preferred embodiment, the element and the section thereof which forms the metacarpal section of the stiff body are elongate. This also comprises the possibility that the entire elongate element forms the metacarpal section. The first end of the metacarpal section is formed by one of the two longitudinal ends of the elongate element, and the metacarpal section has the first end and the second end in the longitudinal direction of the metacarpal section, i.e. the metacarpal section has the first and the second end in the longitudinal direction. The metacarpal section is curved in such a manner that it has the shape of a segment of a noncircular ring which surrounds and defines an elongate and oval or substantially oval ring opening. As already stated, the first end and the second end of the metacarpal section are therefore spaced apart from each other or lie opposite each other at a distance. In other words, the metacarpal section is provided in the shape of an open ring.

The metacarpal section is then furthermore designed in such a manner that said metacarpal section can be brought into engagement with a human hand by said metacarpal section not only being placed in the described manner against the palm of the hand, but at the same time being placed around the back of the hand and the palm of the hand below the metacarpophalangeal joints of an index finger, middle finger, ring finger and small finger (and above or, preferably, below the metacarpophalangeal joint of the thumb) and, because of the elongate design, above the carpus such that said metacarpal section extends in the circumferential direction of the metacarpus around the latter and, in the process, rests completely or partially against the latter and partially embraces the metacarpus. More precisely, said metacarpal section extends in the circumferential direction of the metacarpus or in a direction between the two edges of the hand completely or partially over the back of the hand and, in the process, completely or partially rests against the latter. Furthermore, said metacarpal section runs around one or both edges of the hand and rests completely or partially against one edge of the hand or against both edges of the hand. Finally, said metacarpal section extends in the circumferential direction of the metacarpus or in a direction between the two edges of the hand over the entire palm, or at least part of the palm, and completely or partially rests against the latter. It is preferred in this case if the metacarpal section surrounds the metacarpus in a plane which runs substantially perpendicularly to the longitudinal axis of the forearm in the anatomical normal position of hand and forearm. By means of this configuration of the metacarpal section, the two longitudinal edges of the metacarpal section, when placed on, are advantageously arranged in the region of the metacarpus and are spaced apart from the wrist in the direction of the fingers. Therefore, the wrist is advantageously not covered and remains freely movable.

In addition, it is preferred in this embodiment if the thumb section is elongate and has its first and second end in the longitudinal direction thereof.

In a preferred embodiment, the stiff body is formed in its entirety from the element or elongate element, and the thumb section, like the metacarpal section, is a preferably elongate (partial) section of the element or elongate element. The first end of the metacarpal section is then formed by one end or one of the two longitudinal ends of the stiff body, and the second end of the thumb section corresponds to the opposite end of the stiff body. The thumb section extends from the second end of the metacarpal section, and, for this purpose, the first end of the thumb section is fastened to the first end of the metacarpal section (or can be fastened thereto) or is preferably formed by the second end of the metacarpal section or is identical thereto. In the latter case, the stiff body and the element or the elongate element are in each case of single-piece design.

These two configurations of an orthosis have the advantage of being able to be used to achieve reliable fixing which hardly impairs the functionality of the hand and, in particular, does not restrict the mobility of the wrist. If the metacarpal section is configured in such a manner that, when the orthosis is placed onto the hand, said metacarpal section also runs in the above-described manner over the back of the hand, this part of the metacarpal section that runs over the back of the hand advantageously reliably stabilizes the orthosis during use in the event of an attempt to move the thumb in relation to the thumb section. The same can alternatively also be achieved by a metacarpal section which is configured in such a manner that, when the orthosis is placed against the hand, said metacarpal section does not run over the back of the hand or rests against the latter if the metacarpal section is reliably held in contact with the palm by a suitable closure device or fastening device. As has already been mentioned and as is explained in more detail further below, such a fastening device can have, for example, one or more flexible or elastic bands which, together with the metacarpal section and optionally further sections of the orthosis, when placed on, surround the hand, wherein the bands at least partially run over the back of the hand. The above advantages are realized particularly simply by the design of the metacarpal section and thumb section in the form of parts or sections of a stiff body. A fixing of the thumb in all directions of movement can be achieved, i.e. with respect to rotation, abduction and adduction and also dorsal and palmar flexion. Pinch grip, full mobility of the wrist and can be configured in a simple manner.

In addition, owing to the formation of the metacarpal section and thumb section by a single stiff body, the orthosis can be placed on in a simple manner using one hand. All that is required is to arrange the metacarpal section around the metacarpus and subsequently, or in the process, to arrange and secure the thumb on the thumb section. During the fastening of the metacarpal section to the metacarpus, the thumb section is automatically arranged in the correct position. Furthermore, despite little contact surface, a greater degree of immobilization is achieved in comparison to the prior art.

In a preferred embodiment, a stiffener is provided in the region of the first end of the thumb section and in particular in the transition region between the metacarpal section and the thumb section. If the thumb section extends from the second end of the metacarpal section, such a stiffener is preferably provided in the region of the first end of the thumb section and of the second end of the metacarpal section. As a result, the transition region of metacarpal section and thumb section is reinforced, and therefore, during use, the thumb section is reliably and stably held in the correct position with respect to the metacarpal section. Alternatively or preferably in addition, a reinforcement can also be provided at one or more other points of the stiff body, optionally in a spot wise manner, by means of a suitable profiling or the provision of suitable stiffening materials. Since the body is stiff, such additional stiffeners or reinforcements can be provided without the use of the orthosis by the user and in particular the placing on of the orthosis being impaired, and without disadvantages arising for the user during the wearing of the orthosis.

In a preferred embodiment, a partial region of the stiff body, or the entire stiff body, is plastically deformable for better individual adaptation to the hands of various users. For example, the stiff body can be formed at least in partial regions from one or more materials which permit such a deformation after heating to a certain temperature and, after cooling again, ensure sufficient rigidity and dimensional stability.

In a preferred embodiment, the element or elongate element of the stiff body and/or the thumb section comprise one or more metals, in particular aluminum, and/or one or more plastics materials. If metal is used, in particular aluminum can advantageously be selected, and a thermoplastic elastomer can advantageously be used as the plastic. In a particularly preferred configuration, the element or elongate element and/or the thumb section have a metal core which is covered by a plastics material. For this purpose, the metal core can in particular be insert-molded with the plastics material.

In a preferred configuration of embodiments in which the metacarpal section has the form of a segment of a ring surrounding an elongate ring opening, the metacarpal section is dimensioned in such a manner that said metacarpal section extends over at least 30%, preferably at least 40% and more preferably at least 50% of the circumference of the ring opening which is defined by the ring corresponding to the segment. Secure embracing of the metacarpus and at least a good pre-securing of the orthosis on the hand can thereby be achieved.

It is preferred if the stiff body has padding which can be provided, for example, by textile pads, foam, gel and/or air. The padding is arranged in such a manner that, following fastening to the hand of a user, said padding comes into contact with the hand. The padding can also be configured in such a manner that it cannot only increase the wearing comfort for the user, but also size differences between different hands can also be compensated for to a certain extent with it.

In a preferred configuration of embodiments in which the metacarpal section has the shape of a segment of a ring surrounding an elongate ring opening, the metacarpal section is configured in such a manner that its first and second end lie opposite each other on a long side of the elongate ring opening which is defined by the imaginary, noncircular, elongate ring, of which the segment constituting the metacarpal section is a part. The intermediate space present between the two ends is arranged here in such a manner that, when the orthosis is placed on a hand, said intermediate space is located in the region of the palm. The metacarpal section therefore extends over the entire back of the hand and embraces both edges of the hand. It is of advantage here if, when the orthosis is placed on, the second end of the metacarpal section is arranged in the region of the thumb in order to be able to hold the thumb section in as short and therefore stable a manner as possible.

In this embodiment, the thumb section is furthermore arranged bending down with respect to the course of the metacarpal section, in the region in which the thumb section extends away from the metacarpal section, for example with respect to the course of the metacarpal section at the second end thereof when the thumb section extends from the second end of the metacarpal section. The thumb section preferably extends in the region of its first end substantially perpendicularly to the respective region of the metacarpal section.

In this embodiment, it is furthermore preferred if the thumb holding section is of ring-segment-shaped design and preferably surrounds more than 50% of the circumference of the ring opening, which is defined by the ring corresponding to the ring-segment-shaped thumb holding section, and preferably surrounds more than 60%, more preferably more than 70% and most preferably more than 80%. As a result, when the orthosis is placed on, said thumb holding section embraces more than 50%, preferably more than 60%, more preferably more than 70% and most preferably more than 80% of the circumference of the thumb and thereby prevents an intentional lateral outward movement or at least a lateral slipping out of the thumb. In a particularly advantageous configuration, the thumb holding section is of closed design to an extent such that the thumb can no longer be introduced laterally, but rather only still axially, into the thumb holding section.

In this embodiment, it is also preferred if the metacarpal section runs in a first plane, and the ring-segment-shaped thumb holding section runs in a second plane, wherein the first and second plane are tilted in relation to each other.

In this embodiment, it is also preferred if the metacarpal section has, in the vicinity of its first end, a curvature which, for contact with the depression in the palm of a human hand, protrudes inward for this purpose into the elongate ring opening which is defined by the imaginary, noncircular, elongate ring, of which the segment constituting the metacarpal section is a part. In other words, the curvature is part of the palmar surface of the metacarpal section in the vicinity of the first end thereof which is arranged in the region of the palm when the orthosis is placed onto a hand.

In this embodiment, it is also preferred if the metacarpal section is designed in such a manner that the distance between its surface coming into contact with the back of the hand and its surface coming into contact with the palm increases in the direction of that longitudinal edge of the metacarpal section which faces in the direction of the carpus when the orthosis is placed on. This takes into consideration the shape of human hands which in each case have a curvature at both edges of the hand below the small finger and the index finger, and the shape of the lower thumb region. It is thereby possible to ensure a secure fit solely by the stiff body without additional closure elements.

In this embodiment, it is also preferred if the elongate element has the greatest width, as measured between the two longitudinal edges, at the first end of the metacarpal section, or at least in the vicinity of the first end of the metacarpal section, and tapers in the direction of the opposite end of the elongate element or the second end of the metacarpal section or the second end of the thumb section. The width here can be reduced continuously in particular between the first and the second end. This configuration also contributes to a firm fit of the orthosis, since the configuration prevents the patient, during the attempt to bring his thumb into abduction, from pushing the metacarpal section away from the hand and thereby pushing the hand out of the metacarpal section.

In an alternative preferred configuration of embodiments in which the metacarpal section has the form of a segment of a ring surrounding an elongate ring opening, the metacarpal section is configured in such a manner that its first and second end lie opposite each other in such a manner that at least part of the intermediate space formed therebetween is located on a narrow side of the ring opening which is defined by the ring corresponding to the segment. In addition, this part of the intermediate space, when placed onto a hand, is arranged in the region of the thumb. It is preferred here if at least one end of the metacarpal section is located in the region of the thumb when the orthosis is placed onto a hand. For example, the metacarpal section can be configured in such a manner that its first and second end lie opposite each other on a narrow side of the elongate ring opening which is defined by the imaginary, noncircular, elongate ring, of which the segment constituting the metacarpal section is a part. The intermediate space present between the two ends is then arranged and dimensioned in such a manner that the intermediate space and the first and second end of the metacarpal section are located in the region of the thumb and advantageously in the region of the edge of the hand when the orthosis is placed onto a hand. The metacarpal section therefore extends completely or at least partially over the back of the hand and embraces the edge of the hand lying opposite the thumb. The first end, and preferably also the second end, of the metacarpal section, when placed on, are arranged in the region of the carpometacarpal joint. In other words, the metacarpal section is configured in such a manner that, when the orthosis is placed onto a hand, said metacarpal section extends away from the palm in the vicinity of the carpometacarpal joint of the thumb around the edge of the hand and over part of the back of the hand or over the back of the hand, where the first end is then arranged, for example into the vicinity of the carpometacarpal joint.

In this embodiment, the thumb section is furthermore arranged such that said thumb section, at least in the region of its first end, runs in the same or substantially same direction as the metacarpal section in the region of the second end thereof and extends away from the metacarpal section. In other words, the thumb section is a continuous extension or a continuous continuation of the metacarpal section and does not bend down differently than in the preceding embodiment.

In this embodiment, it can be provided in preferred configurations that, as indicated above for the preceding alternative embodiment, the thumb holding section is of ring-segment-shaped design and surrounds more than 50% of the circumference of the ring opening which is defined by the ring corresponding to the ring-segment-shaped thumb holding section, that the metacarpal section and the ring-segment-shaped thumb holding section run in planes tilted in relation to each other, that the distance between the surface of the metacarpal section that comes into contact with the back of the hand and the surface thereof which comes into contact with the palm increases in the direction of that longitudinal edge of the metacarpal section which, when the orthosis is placed on, faces in the direction of the carpus, and/or that the elongate element has the greatest width, as measured between the two longitudinal edges, at the first end of the metacarpal section or at least in the vicinity of the first end of the metacarpal section and tapers in the direction of the opposite end of the elongate element or the second end of the metacarpal section or the second end of the thumb section. The same details and advantages as have been explained above for the alternative embodiment apply in this regard.

In addition, it can also be advantageously provided in this embodiment that the metacarpal section has a curvature which, for contact with the depression in the palm of a human hand, protrudes inward for this purpose into the elongate ring opening which is defined by the imaginary, noncircular, elongate ring, of which the segment constituting the metacarpal section is a part. In other words, the curvature is part of the palmar surface of the metacarpal section, which part is arranged in the region of the palm when the orthosis is placed onto a hand.

In this embodiment, it is furthermore preferred if the orthosis contains a closure element for securing the orthosis, said closure element having a band which is preferably provided with a touch and close element.

The band of such a closure element can be fastened preferably by one end to the thumb section. Said band is configured and fastened or can be fastened here in such a manner that, when the orthosis is placed onto a hand, said band can be guided around the thumb, which is arranged in the thumb holding section, in such a manner that said band entirely or at least partially surrounds the circumference of the thumb holding section. In the case of the ring-segment-shaped thumb holding section, the band is preferably configured and fastened or can be fastened in such a manner that, when the orthosis is placed onto a hand, said band can be guided around the thumb arranged in the thumb holding section in such a manner that the intermediate space between the two longitudinal ends of the ring-segment-shaped thumb holding section is spanned and the combination of thumb holding section and band is annularly closed. The band here can preferably be brought in this region into contact with the thumb. It is preferred in this connection if that end of the band which is fastened to the thumb section is or can be fastened to the convex surface of the thumb holding section, advantageously in such a manner that the band runs in the vicinity of this end along the convex surface and is fastened or can be fastened to the latter. In order to surround the thumb, the band then only has to be guided in a manner continuing this course and optionally over the intermediate space between the two longitudinal ends of the ring-segment-shaped thumb holding section, which intermediate space is then spanned by the band.

In the case of the above embodiments with a closure element having a band, it is furthermore preferred if the band is configured and fastened or can be fastened in such a manner that, when the orthosis is placed on, said band can be guided completely around the thumb and over the metacarpophalangeal joint and the dorsal side of the thumb and, at its end opposite the end fastened to the thumb section, can be fastened to a section of the metacarpal section that is arranged in the region of the back of the hand when the orthosis is placed onto a hand. If the band has a touch and close fastening element, a corresponding touch and close fastened element is preferably arranged on this section of the metacarpal section.

In a preferred embodiment, the metacarpal section is designed in such a manner that it rests against a human hand exclusively in the region of the palm when the orthosis has been placed correctly onto the hand. As has already been explained above, when the orthosis has been placed on, the metacarpal section has firstly been brought into engagement with the hand such that said metacarpal section rests against the palm of the hand below the metacarpophalangeal joint of an index finger, middle finger, ring finger and small finger and extends in a direction between the two edges of the hand over at least part of the palm and at least partially rests against the latter. Secondly, the thumb section has been placed on the thumb of the hand such that the thumb is arranged in the ring opening defined by the thumb holding section, and the thumb holding section extends over at least part of the circumference of the thumb and at least partially surrounds the latter.

In other words, the metacarpal section is designed in such a manner that, when placed onto the hand, said metacarpal section does not extend over parts of the back of the hand and preferably also does not extend over one or both edges of the hand.

Furthermore, the orthosis in this embodiment has a closure device or fastening device for fastening the orthosis when placed on the hand. The closure device has one or more first fastening sections which are arranged and configured in such a manner that, when the orthosis is placed on, said fastening sections can be arranged and secured on the metacarpal section and/or the thumb section in such a manner that said fastening sections in each case run over the back of the hand and, together with the metacarpal section, forms at least a part of a section of the orthosis, which section annularly surrounds the hand. The orthosis can thereby be simply and securely held or secured on the hand by the first fastening section or the first fastening sections— either by themselves or together with further sections of the closure device. This closure device or fastening device or at least the first fastening sections or at least one of the first fastening sections can either be provided as separate components which can be completely detached from the metacarpal section and the thumb section or the rest of the orthosis and can be connected again thereto for fastening purposes, or as components which are fastened permanently to the metacarpal section, the thumb section and/or to another part of the orthosis. In the latter case, it can be provided in particular that the relevant first fastening sections are in each case permanently fastened at one point and, after arrangement such that they run over the back of the hand, can be fastened releasably for securing at another point.

First fastening sections of this type can be formed in an advantageous manner, for example, by a respective flexible and/or elastic band. In one configuration, the bands can in each case be fastened at one end to the metacarpal section or the thumb section and adapted in order to be connected releasably at a distance from said end to the first end of the metacarpal section. In particular, each of said bands is preferably arranged in such a manner that, when the orthosis is placed on, said band can be guided from its end fastened to the metacarpal section or to the thumb section over the back of the hand, in a manner resting thereagainst, to the first end of the metacarpal section. For the releasable connection to the first end of the metacarpal section, the bands can in each case have touch and close elements which can interact with corresponding, suitably arranged, different touch and close elements on the bands themselves or on the metacarpal section or on another part of the orthosis. In this connection, one or more openings, through which one or more of the bands can guided in each case, can be provided at the first end or on a section connected to the latter. After passing through, each band can be fastened, for example, to itself, for example with the aid of the abovementioned touch and close elements, thus in each case producing a loop section which runs through one of the openings.

The above embodiment has the advantage that, on the basis of limiting the size of the stiff metacarpal section, the weight can be kept low and the orthosis can be particularly agreeable to wear.

In this embodiment, it is furthermore preferred if the thumb holding section is of ring-segment-shaped design. It can advantageously be provided here that said thumb holding section comprises more than 50% of the circumference of the ring opening which is defined by the ring corresponding to the ring-segment-shaped thumb holding section, and preferably comprises more than 60%, more preferably more than 70% and most preferably more than 80%. As a result, when the orthosis is placed on, said thumb holding section embraces more than 50%, preferably more than 60%, more preferably more than 70% and most preferably more than 80% of the circumference of the thumb and thereby prevents an intentional lateral outward movement or at least a lateral slipping out of the thumb. In a particularly advantageous configuration, the thumb holding section is of closed design to an extent such that the thumb can no longer be introduced laterally, but only still axially, into the thumb holding section.

In this embodiment and in particular in the case of the ring-segment-shaped configuration of the thumb holding section, it is also preferred if the closure device furthermore has one or more second fastening sections which are in each case arranged and configured such that, when the orthosis is placed on, said fastening sections can be at least partially guided around the thumb in such a manner that they annularly surround the thumb together with the thumb holding section. Second fastening sections of this type can be formed in an advantageous manner, for example, by a respective flexible and/or elastic band. Said fastening sections can be fastened in particular by one end to the thumb section and can have, for example, a touch and close element with which said fastening sections, after being guided around the thumb, can be secured, in particular with the use of a corresponding, suitably arranged, other touch and close element.

In this embodiment, it is furthermore preferred if the metacarpal section has a first surface for contact with the palm and an opposite, second surface which, when the orthosis is put on, is directed away from the hand, wherein the first surface has two concave sections and a convex section arranged between the latter, between the first end and second end of the metacarpal section. The first surface then constitutes a palmar surface or contact surface. As a result, a particularly good contact with the palm of a human hand and, accordingly, a particularly good contact and supporting effect are possible, in particular because the first surface corresponds, by means of the curvature provided with the convex section and the concave section adjacent to said curvature on both sides, to the anatomical shape of a palm with a depression between the end of the petering-out ball of the thumb and the section in the vicinity of the opposite edge of the hand. It is furthermore preferred here if, in each of the two concave sections, a passage opening is formed in the first surface and through the metacarpal section. This improves the wearing comfort and further reduces the weight of the orthosis. The passage openings preferably have radial dimensions which are larger than the radial dimensions of those regions of the metacarpal section, of the stiff body or of the orthosis that surround the passage openings. The passage openings are preferably arranged and adapted for partially accommodating part of the ball of the thumb or a section in the vicinity of the opposite edge of the hand.

In addition, in this embodiment, in the region of the convex section, the metacarpal section can have a tapered portion in a direction traversely with respect to the direction between the first and second end of the metacarpal section and along the first surface, i.e. perpendicular to an edge or border surface of the metacarpal section, said edge or border surface connecting the first and second surface. In other words, the metacarpal section, optionally together with a section of the orthosis that is adjacent to the first end of the metacarpal section, has the shape of an "8" or of a "B" in a top view of the first surface. It has been shown that, as a result, the contact and the supporting effect can be improved even further and the metacarpal section can be reliably prevented from lifting off during movement of the hand.

In this embodiment, it is furthermore preferred if the metacarpal section merges at its first end into a flexible section, wherein the flexible section is preferably of single-piece design with the metacarpal section. For example, the flexible section and the metacarpal section or the flexible section and the stiff body can be formed by a single component or a single body, in particular by a single component or plastics component, in the interior of which stiffening elements are arranged overall or substantially overall, with the exception of the flexible section, or which is stiffened overall or substantially overall, with the exception of the flexible section, in another manner. The flexible section permits better adaptation to a human hand, in particular in the region of the edge of the hand. It is especially preferred if the first fastening sections, for example as bands in the above-described configuration, can be connected to the first end of the metacarpal section via the flexible section by the flexible section having a device for the releasable fastening of the first fastening sections to the flexible section. Said device can have, for example, one or more passage openings through which the first fastening sections can be guided.

BRIEF DESCRIPTION OF THE DRAWING

The invention is explained in more detail below using exemplary embodiments with reference to the drawings.

DETAILED DESCRIPTION OF THE INVENTION

Figure 1:
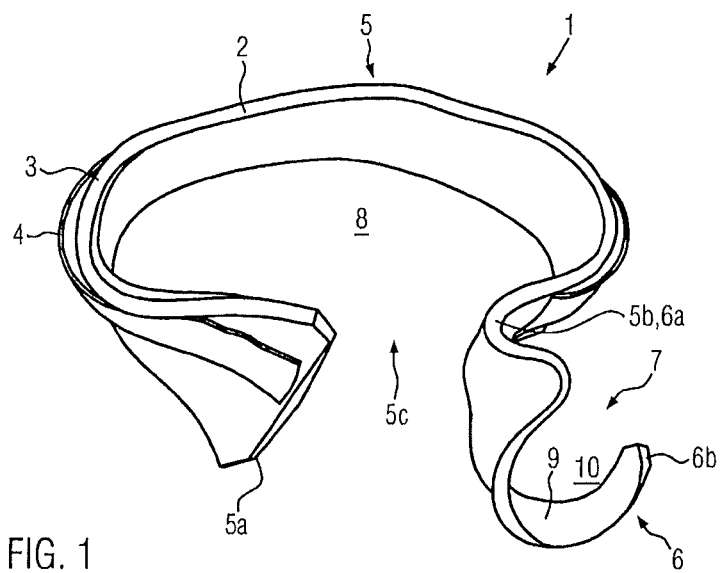
FIG. 1 shows a perspective view of a first embodiment of the orthosis according to the invention.
Figure 2:
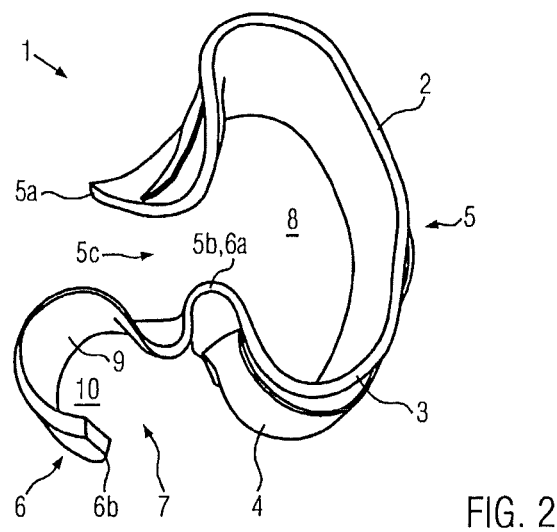
FIG. 2 shows a further perspective view of the first embodiment of the orthosis according to the invention.

FIGS. 1 and 2 show perspective views of a first embodiment of an orthosis 1 which is adapted for fastening to a human hand in order, when placed onto the hand, to fix the carpometacarpal joint and metacarpophalangeal joint of the thumb of the hand.

The orthosis 1 consists of a flat, band-shaped and curved, stiff body 2 in the form of an elongate element. The stiff body or the elongate element 2 has a stiff plastics element 3 and a reinforcing strip 4 which is formed from aluminum and is attached or integrated along part of the plastics element 3.

The stiff body 2 and therefore the orthosis 1 firstly have a carpometacarpal section 5 which is provided in the form of an open and approximately oval ring for receiving the metacarpus of a human hand, and secondly have a thumb section 6 with a ring-segment-shaped thumb holding section 7 for receiving the thumb of the hand. The flat, band-shaped body 2 is curved in order to form the orthosis 1 in such a manner that part of an expanded side of the body 2 forms the inner side or inner surface of the metacarpal section 5, said inner side or inner surface being provided for contact with a metacarpus, and part of the opposite expanded side of the body 2 forms the inner side or inner surface of the ring-segment-shaped thumb holding section 7, said inner side or inner surface being provided for contact with a thumb. In other words, the narrow longitudinal edges of the body 2 are aligned in the axial direction of the metacarpal section 5.

The metacarpal section 5 has a first end 5a and a second end 5b, which lie opposite each other separated by an intermediate space 5c in order to form the open ring. The end 5a is identical to a longitudinal end of the body 2, and the metacarpal section 5 is formed by an elongate partial section of the elongate body 2. The elongate and substantially oval interior space 8 defined by the metacarpal section 5 has the typical cross-sectional shape of a human metacarpus. The two ends 5a and 5b and the intermediate space 5c are arranged on one of the two expanded sides of the interior space 8, and therefore the opposite expanded side of the interior space 8 is continuously limited by the body 2.

The rest of the body 2 forms the thumb section 6 which is therefore a further elongate partial section of the body 2 that directly adjoins the partial section forming the metacarpal section 5. In other words, the thumb section 6 emerges from the second end 5b of the metacarpal section 5 and has a first end 6a and a second end 6b, wherein the first end 6a coincides with the second end 5b of the metacarpal section 5, and the second end 6b of the thumb section 6 is identical to a longitudinal end of the body 2. The thumb section 6 extends substantially perpendicularly from the metacarpal section 5 and, in the vicinity of its second end 6b, has the ring-segment-shaped thumb holding section 7 which has a concave supporting surface 9 for contact with a thumb and defines an interior space 10 for receiving the thumb. The ring-segment-shaped thumb holding section 7 is arranged in such a manner that the interior space 10 is opened laterally in a direction away from the first end 5a of the metacarpal section 5.

Figure 3:
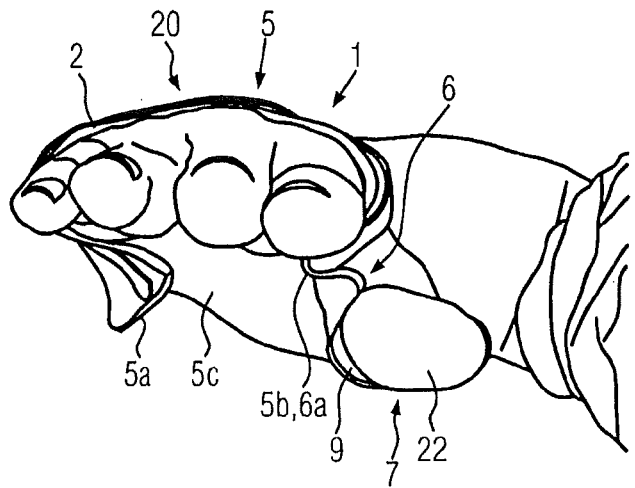
FIG. 3 shows a view from above of the fingertips of a hand onto which the first embodiment of the orthosis according to the invention is placed.
Figure 4:
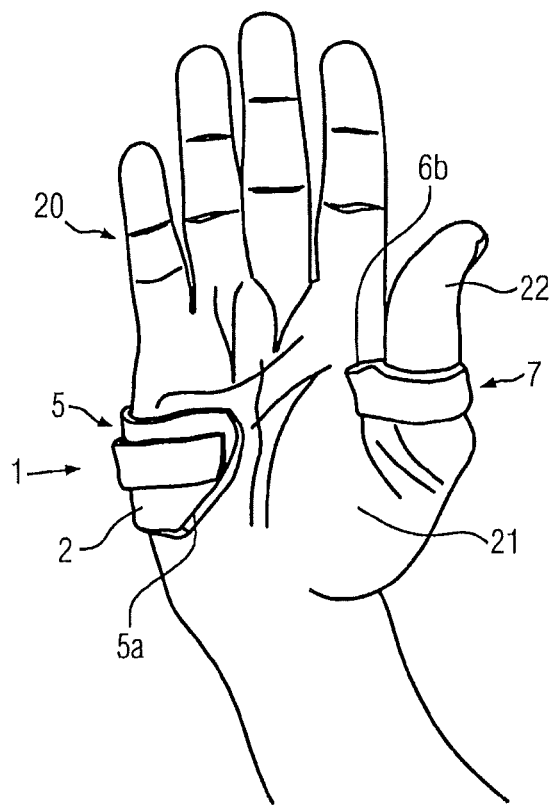
FIG. 4 shows a view of the palm of the hand with the orthosis according to the first embodiment placed thereon.
Figure 5:
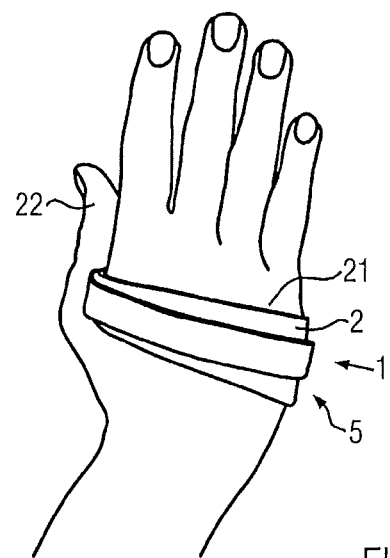
FIG. 5 shows a view of the back of the hand with the orthosis according to the first embodiment placed thereon.
Figure 6:
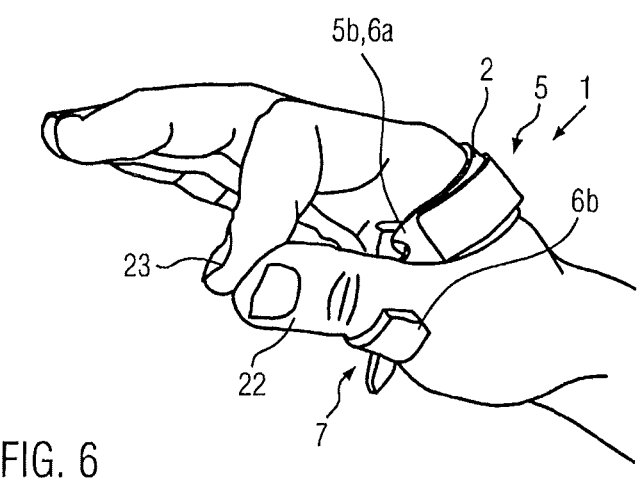
FIG. 6 shows a view of the thumb and index finger side of the hand with the orthosis according to the first embodiment placed thereon.

FIG. 3 shows the course of the body 2 of the orthosis 1 after the orthosis 1 has been placed onto a human hand 20 and, more precisely, has been placed around the metacarpus 21 and the thumb 22 of the hand 20 (see FIGS. 4 to 6). In order to ensure that the body 2 rests along most of its length against the hand 20, the body 2 is provided with a certain degree of elasticity.

The first end 5a is arranged on the palm of the hand 20 in the region of the small finger and ring finger, and the elongate section of the body 2 that forms the metacarpal section 5 runs from there around the outer edge of the hand, over the entire back of the hand and around the inner edge of the hand, and the second end 5b of the metacarpal section 5 is arranged on the palm of the hand 20 in the region of the thumb and index finger. Owing to the certain degree of elasticity of the metacarpal section 5, the intermediate space 5c has been slightly expanded when the orthosis 1 was placed onto the hand 20, and the metacarpal section 5 rests substantially along its entire length against the metacarpus 21.

The thumb section 6 extends outward substantially perpendicularly from the metacarpal section 5, and therefore the ring-segment-shaped thumb holding section 7 is aligned in such a manner that the thumb 22 of the hand 20 can be arranged in the interior space 10 defined by the thumb holding section 7 and the inner side of the thumb 22 can be placed onto the supporting surface 9. It is preferred if the ring-segment-shaped thumb holding section 7 is closed to such an extent that, after the orthosis 1 has been placed on, the thumb 22 can no longer readily be moved laterally out of the orthosis. For this purpose, it is preferred if the ring-segment-shaped thumb holding section 7 extends over an angle of more than 180° and embraces more than 50% of the circumference of the thumb 22. For the placing-on of the orthosis 1, it then has to be provided that the thumb holding section 7 can be sufficiently elastically expanded so as to be placed on, or that the thumb 22 has to be introduced from below in the axial direction into the interior space 10 so as to be placed on. Separate closure elements for securing the orthosis 1 on the hand 20 are then not required.

FIGS. 4 and 5 show respective views of the palm and the back of the hand 20 with the orthosis 1 placed thereon. It can be seen that the metacarpal section 5 extends completely over the back of the hand and embraces the edges of the hand on both sides. By means of the arrangement of the thumb holding section 7 and the alignment of the supporting surface 9, a support of the thumb 22 with respect to a movement in the direction of the palm is provided, inter alia. Nevertheless, the important pinch grip, in which the index finger 23 is brought into contact with the thumb 22, can be carried out (see FIG. 6).

Figure 7:
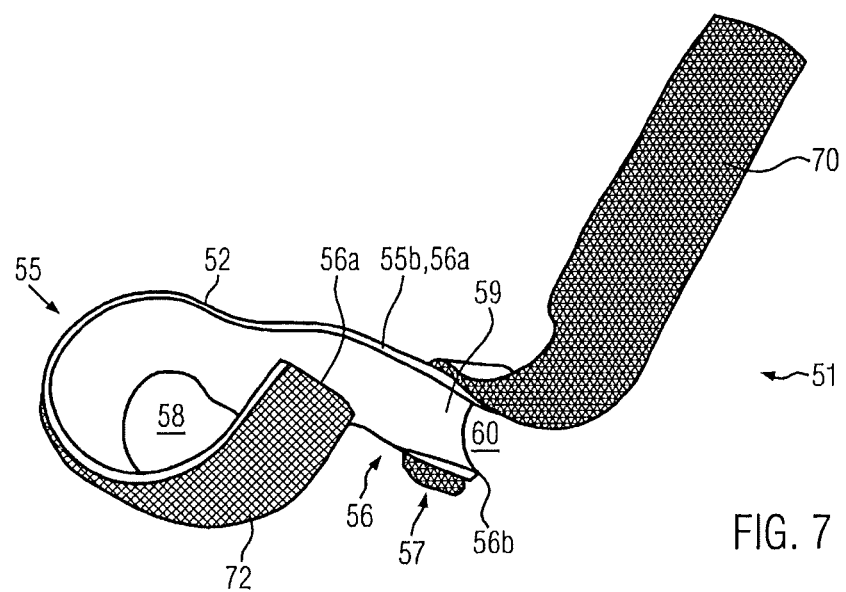
FIG. 7 shows a perspective view of a second embodiment of the orthosis according to the invention.
Figure 8:
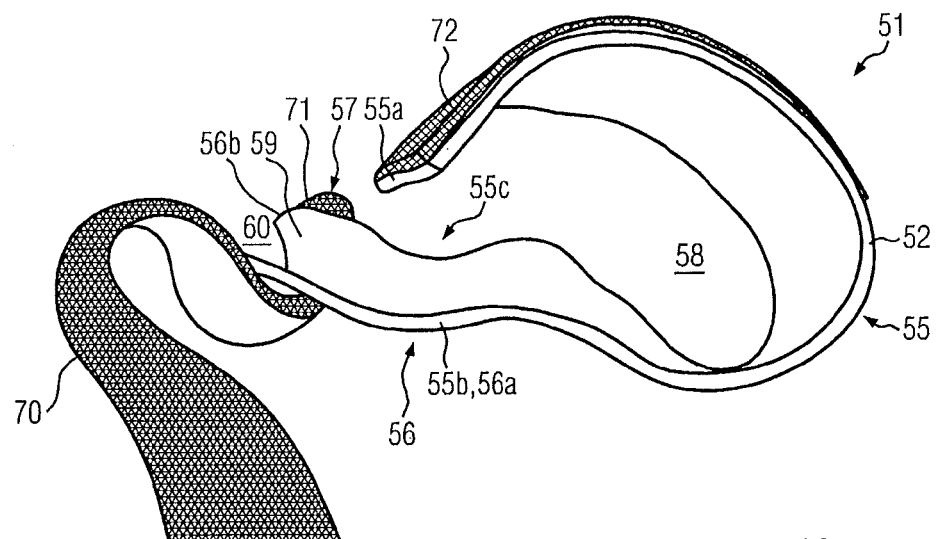
FIG. 8 shows a further perspective view of the second embodiment of the orthosis according to the invention.

FIGS. 7 and 8 show perspective views of a second embodiment of an orthosis 51 which is adapted for fastening to a human hand in order, when placed onto the hand, to fix the carpometacarpal joint and metacarpophalangeal joint of the thumb of the hand.

The orthosis 51, like the orthosis 1, has a flat, band-shaped and curved stiff body 52 in the form of an elongate element. The stiff body or the elongate element 52 is formed from a plastics material. For reinforcement purposes, a reinforcing element made from aluminum can be provided, for example, in the interior of said body.

The basic design of the orthosis 51 and of the body 52 corresponds to the configuration of the orthosis 1 and of the body 2.

Accordingly, the stiff body 52 and therefore the orthosis 51 firstly have a carpometacarpal section 55 which is provided in the form of an open and approximately oval ring for receiving the metacarpus of a human hand, and secondly have a thumb section 56 with a ring-segment-shaped thumb holding section 57 for receiving the thumb of the hand. The flat, band-shaped body 52 is curved in order to form the orthosis 51 in such a manner that part of an expanded side of the body 52 forms the inner side or inner surface of the metacarpal section 55, said inner side or inner surface being provided for contact with a metacarpus, and part of the opposite expanded side of the body 52 forms the inner side or inner surface of the ring-segment-shaped thumb holding section 57, said inner side or inner surface being provided for contact with a thumb. In other words, the narrow longitudinal edges of the body 52 are aligned in the axial direction of the metacarpal section 55.

The metacarpal section 55 here has a first end 55a and a second end 55b, which lie opposite each other separated by an intermediate space 55c in order to form the open ring. The end 55a is identical to a longitudinal end of the body 52, and the metacarpal section 55 is formed by an elongate partial section of the elongate body 52. The elongate and substantially oval interior space 58 defined by the metacarpal section 55 has the typical cross-sectional shape of a human metacarpus.

However, in contrast to the case of the orthosis 1, the two ends 55a and 55b and the intermediate space 55c are arranged on one of the two short sides of the interior space 58.

The rest of the body 52 in turn forms the thumb section 56 which is therefore a further elongate partial section of the body 52 that directly adjoins the partial section forming the metacarpal section 55. In other words, the thumb section 56 emerges from the second end 55b of the metacarpal section 55 and has a first end 56a and a second end 56b, wherein the first end 56a coincides with the second end 55b of the metacarpal section 55, and the second end 56b of the thumb section 56 is identical to a longitudinal end of the body 52. In a different manner than in the case of the orthosis 1, the thumb section 56 extends substantially in the same direction as the metacarpal section 55 at the second end 55b thereof. Said thumb section, in the vicinity of its second end 56b, has the ring-segment-shaped thumb holding section 57 which has a concave supporting surface 59 for contact with a thumb and defines an interior space 60 for receiving the thumb.

The thumb section 56 is designed overall in the manner of a splint onto which a thumb can be placed along most of its length beginning with the metacarpophalangeal joint of the thumb. The supporting surface 59 of the thumb holding section 57 extends from the latter over the rest of the thumb section 56. The ring-segment-shaped thumb holding section 57, and the thumb section 56 overall, is arranged here such that the interior space 60 is open laterally in a direction toward the first end 55a of the metacarpal section 55.

A touch and close band 70 is fastened to the thumb holding section 57, specifically in such a manner that its one end is aligned with a longitudinal end of the ring-segment-shaped thumb holding section 57, and the touch and close band 70 is fastened to the thumb holding section 57 along the entire outer surface thereof, which outer surface is opposite the supporting surface 59. For this purpose, a touch and close element 71 is attached to said outer surface. A further touch and close element 72 is attached along part of the outer surface of the metacarpal section 55, specifically in the vicinity of the end 55a.

Figure 9:
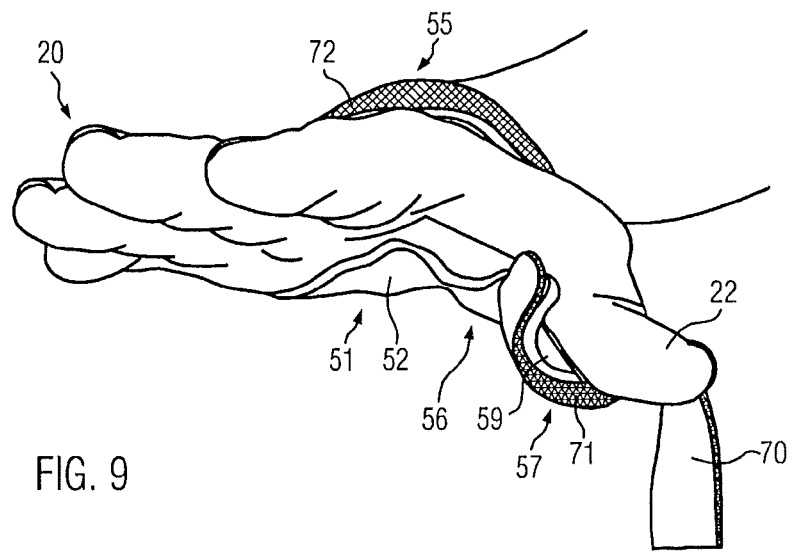
FIG. 9 shows a perspective view from above of the fingertips of a hand onto which the second embodiment of the orthosis according to the invention is placed.
Figure 10:
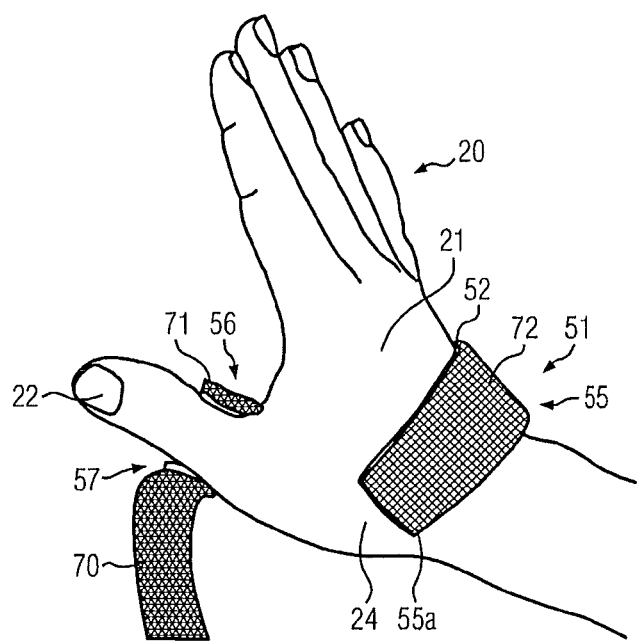
FIG. 10 shows a perspective lateral view of the hand with the orthosis according to the second embodiment placed thereon, with a completely open closure element.

The course of the body 52 of the orthosis 51 after the latter is placed onto a human hand 20, and more precisely around the metacarpus 21 and the thumb 22 of the hand 20, is apparent from FIGS. 9 and 10. In order to ensure that the body 52 can rest along most of its length against the hand 20, the body can likewise be provided with a certain degree of elasticity.

The first end 55a is arranged on the back of the hand 20 in the region of the carpometacarpal joint 24, and the elongate section of the body 52 that forms the metacarpal section 55 runs from there over the back of the hand in the direction of the outer edge of the hand, around said edge of the hand and over the palm in the direction of the inner edge of the hand, and the second end 55b of the metacarpal section 55 is arranged on the palm of the hand 20 in the region of the carpometacarpal joint 24. The metacarpal section 55 is anatomically preshaped corresponding to the typical shape of a human metacarpus, and, owing to a certain degree of elasticity of the metacarpal section 55, the intermediate space 55c has been slightly expanded when the orthosis 51 was placed onto the hand 20. After the final fastening of the orthosis 51 with the aid of the touch and close band 70, the metacarpal section 55 rests substantially along its entire length against the metacarpus 21.

The thumb section 56 extends outward from the metacarpal section 55 substantially as an extension of the palm, and therefore the thumb section 56, and in particular the ring-segment-shaped thumb holding section 57, is aligned in such a manner that the thumb 22 of the hand 20 can be placed onto the thumb section 56 and can be arranged in the interior space 60 defined by the thumb holding section 57, and that the inner side of the thumb 22 can be placed here onto the supporting surface 59. Otherwise, the same considerations as for the thumb holding section 7 of the orthosis 1 apply to the configuration of the ring-segment-shaped thumb holding section 57.

Figure 11:
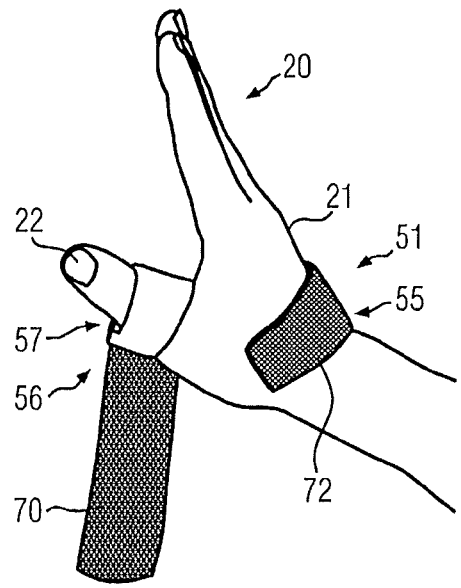
FIG. 11 shows a side view of the hand with the orthosis according to the second embodiment placed thereon, with a partially closed closure element.
Figure 12:
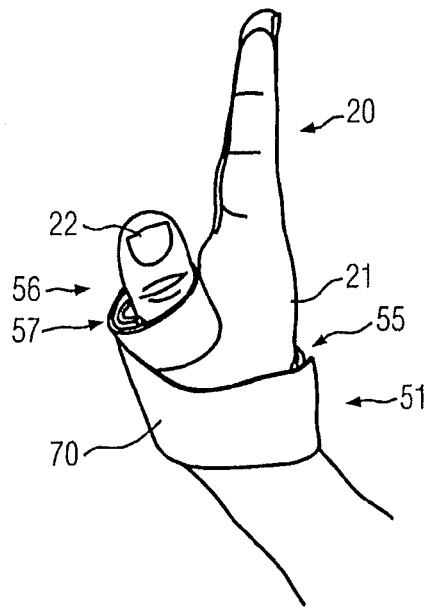
FIG. 12 shows a side view of the hand with the orthosis according to the second embodiment placed thereon, with a completely closed closure element.

However, because of the provision of the touch and close band 70, it is not required, but is possible, for the ring-segment-shaped thumb holding section 57 to extend over an angle of more than 180°. In order to secure the orthosis 51 on the hand 20, the touch and close band 70 is placed over the lateral opening in the ring-segment-shaped thumb holding section 57 in a first step (see FIG. 11). The touch and close band 70 is subsequently guided in the direction of the first end 55a of the metacarpal section 55 and fastened under tension to the touch and close element 72 (see FIG. 12).

Figure 13:
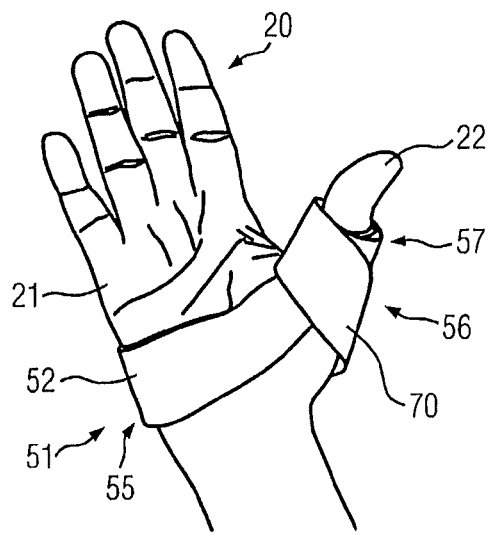
FIG. 13 shows a view of the palm of the hand with the orthosis according to the second embodiment placed thereon.
Figure 14:
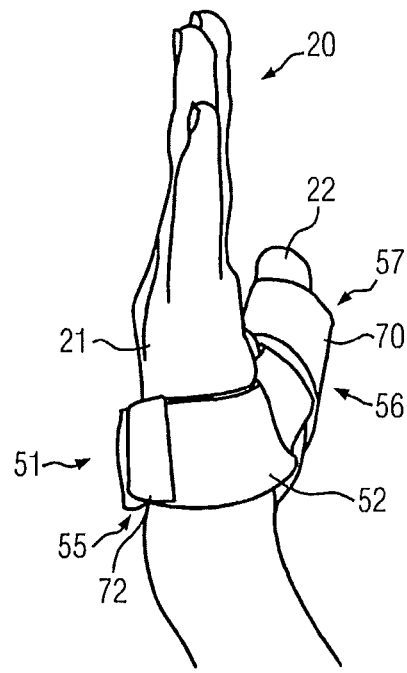
FIG. 14 shows a view of the thumb-remote edge of the hand with the orthosis according to the second embodiment placed thereon.

FIGS. 13 and 14 show views of the palm or the outer edge of the hand 20 with the orthosis 51 placed thereon and fastened by the touch and close band 70. It can be seen that the metacarpal section 55 extends completely over the palm and embraces the outer edge of the hand. By means of the arrangement of the thumb section 56, and in particular of the thumb holding section 57, and the alignment of the supporting surface 59, support of the thumb 22 with respect to a movement in the direction of the palm is again provided, inter alia. Nevertheless, the important pinch grip can be carried out.

Figure 15:
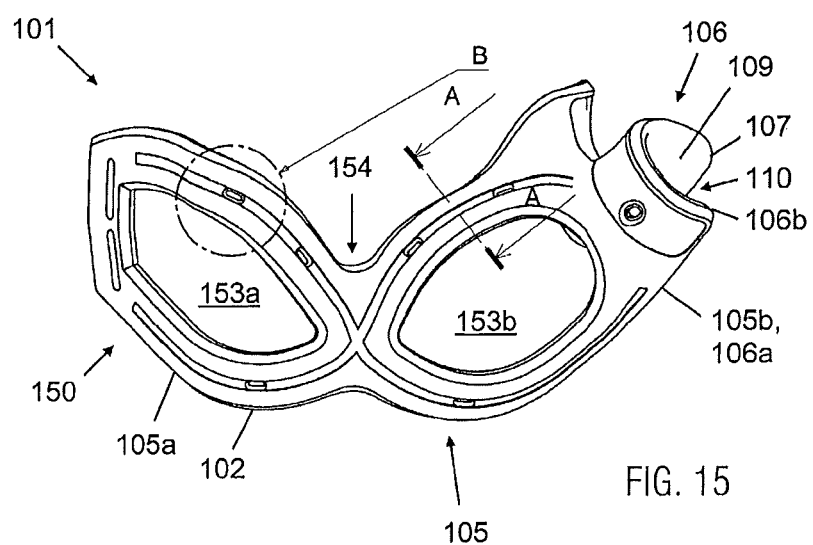
FIG. 15 shows a perspective view of a third embodiment of the orthosis according to the invention.
Figure 16:
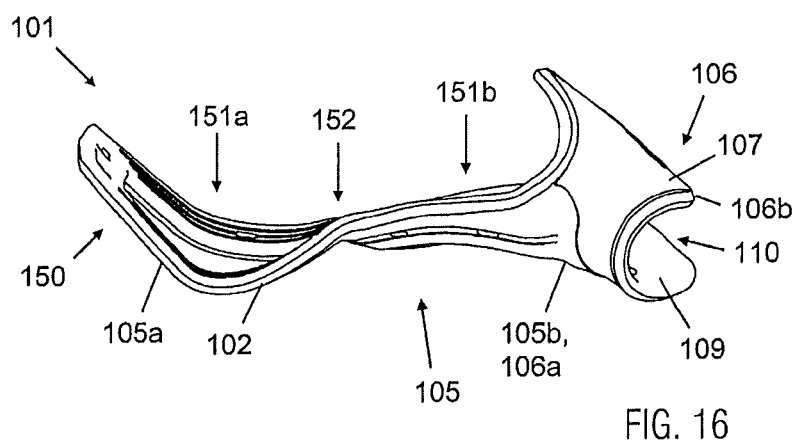
FIG. 16 shows a further perspective view of the third embodiment of the orthosis according to the invention.
Figure 17:
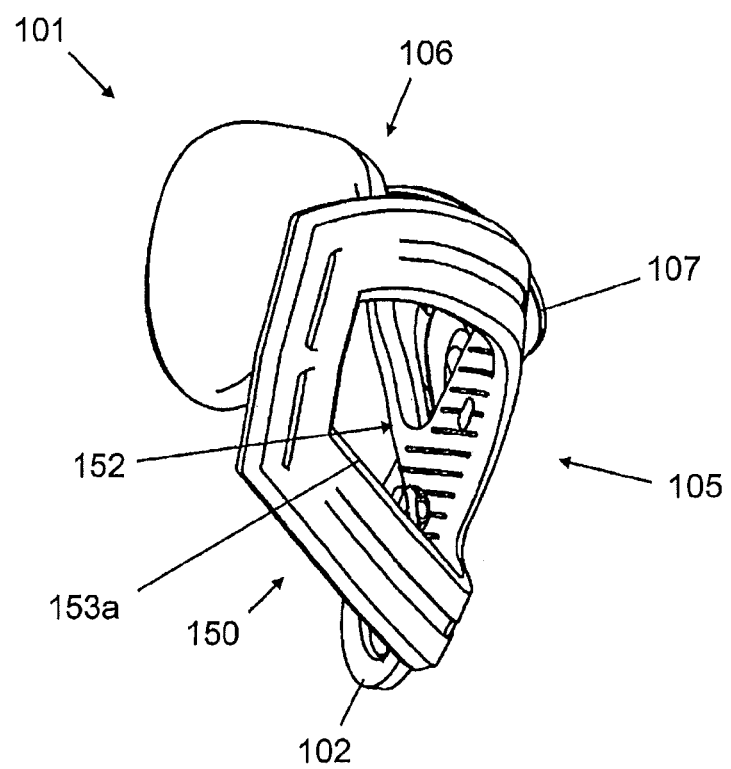
FIG. 17 shows a further perspective view of the third embodiment of the orthosis according to the invention.

FIGS. 15 to 18 show perspective views of a third embodiment of an orthosis 101 which is adapted for fastening to a human hand in order, when placed onto the hand, to fix the carpometacarpal joint and metacarpophalangeal joint of the thumb of the hand. The orthosis 101 is shown in FIGS. 15 to 17 in a variant without closure elements and in FIG. 18 in a different variant with fastening bands. Fastening bands which can be configured, for example, in the same manner as the fastening bands shown in FIG. 18, but are not shown in FIGS. 15 to 17, are likewise provided in the first variant and, when the orthosis 101 is used, have to be connected to the rest of the orthosis 101. With the exception of the fastening bands, the orthosis 101 has precisely the same construction and configuration in both variants, and therefore said variants are only differentiated below with respect to the fastening bands.

The orthosis 101 has a flat, band-shaped and curved, stiff body 102 in the form of an elongate element. The stiff body or the elongate element 102 is formed from a plastics material. For reinforcement purposes, a reinforcing element made from aluminum can be provided, for example, in the interior of said body.

The basic design of the orthosis 101 and of the body 102 corresponds to the configuration of the orthoses 1 and 51 and of the bodies 2 and 52. Accordingly, the stiff body 102 and therefore the orthosis 101 firstly have a metacarpal section 105 and secondly a thumb section 106 with a ring-segment-shaped thumb holding section 107 for receiving the thumb of the hand.

In contrast to the preceding embodiments, the metacarpal section 105 is, however, dimensioned in such a manner that, after being correctly placed onto the palm of a hand, said metacarpal section does not run over the back of the hand. The flat, band-shaped body 102 here is curved in order to form the orthosis 101 in such a manner that part of an expanded side of the body 102 forms both the inner side or inner surface of the metacarpal section 105, which inner side or inner surface is provided for contact with the palm of a metacarpus (and is referred to below as the palmar surface), and the inner side or inner surface of the ring-segment-shaped thumb holding section 107, which inner side or inner surface is provided for contact with a thumb. The narrow longitudinal edges of the body 102 are aligned in the axial direction of the metacarpal section 105.

The metacarpal section 105 has a first end 105a and a second end 105b which is spaced apart from the latter. The end 105a is identical to a longitudinal end of the body 102, and the metacarpal section 105 is formed by an elongate partial section of the elongate body 102.

The first end 105a of the body 102 is adjoined in one piece by a flexible section 150. For this purpose, the body 102 and the flexible section 150 are formed, for example, by a single flexible plastics element, wherein a reinforcement or stiffener is provided in the plastics element in the region of the body 102 in order to form the latter.

The rest of the body 102 in turn forms the thumb section 106 which is therefore a further, optionally likewise elongate, partial section of the body 102 that directly adjoins the partial section forming the metacarpal section 105. In other words, the thumb section 106 emerges from the second end 105b of the metacarpal section 105 and has a first end 106a and a second end 106b, wherein the first end 106a coincides with the second end 105b of the metacarpal section 105, and the second end 106b of the thumb section 106 is identical to a longitudinal end of the body 102. As in the case of the orthosis 51, the thumb section 106 extends substantially in the same direction as the metacarpal section 105 at the second end 105b thereof. Said thumb section has, in the vicinity of its second end 106b, the ring-segment-shaped thumb holding section 107 which has a concave supporting surface 109 for contact with a thumb and defines an interior space 110 for receiving the thumb.

The thumb section 106 provides a splint onto which a thumb can be placed along part of its length beginning with the metacarpophalangeal joint. The supporting surface 109 of the thumb holding section 107 extends from the latter over the rest of the thumb section 106. The ring-segment-shaped thumb holding section 107, and the thumb section 106 overall, is arranged here in such a manner that the interior space 110 is opened laterally in a direction toward the first end 105a of the metacarpal section 105, specifically on that side of the body 102 on which the palmar surface is also located.

The metacarpal section 105 is curved in such a manner that the palmar surface is provided with two concave sections 151a, 151b and, between the latter, in the direction from the first end 105a to the second end 105b, with a convex section 152 (also see FIG. 17). The convex section 152, after being placed onto a hand, provides a curvature which corresponds to the depression in the palm between the end of the petering-out ball of the thumb and the section in the vicinity of the opposite edge of the hand, and the concave sections 151a, 151b correspondingly to the hand structure adjacent to the depression. As a result, the metacarpal section 105 can rest tightly and securely against the palm.

In order to improve the wearing comfort and to reduce the weight of the orthosis 101, respective passage openings 153a, 153b (round openings) through the metacarpal section 105 are formed in the region of the concave section 151a, 152b, wherein the passage opening 153a also partly runs through the flexible section 150 and is limited by the latter. In addition, the metacarpal section 105 has a constriction or tapered portion 154 on the two longitudinal edges in the region of the convex section 152, by means of which constriction or tapered portion the metacarpal section 105 together with the flexible section 150 has the shape of an "8" or of a "B" or is spectacles-shaped, wherein the passage openings 153a, 153b are preferably limited by rings which are narrower in comparison to the diameter of said passage openings and are formed by the metacarpal section 105 and possibly adjacent sections of the orthosis, such as the thumb section 106 and/or the flexible section 150. The provision of the tapered portion 154 makes it possible to counteract the metacarpal section 105 lifting off during hand movements.

Figure 18:
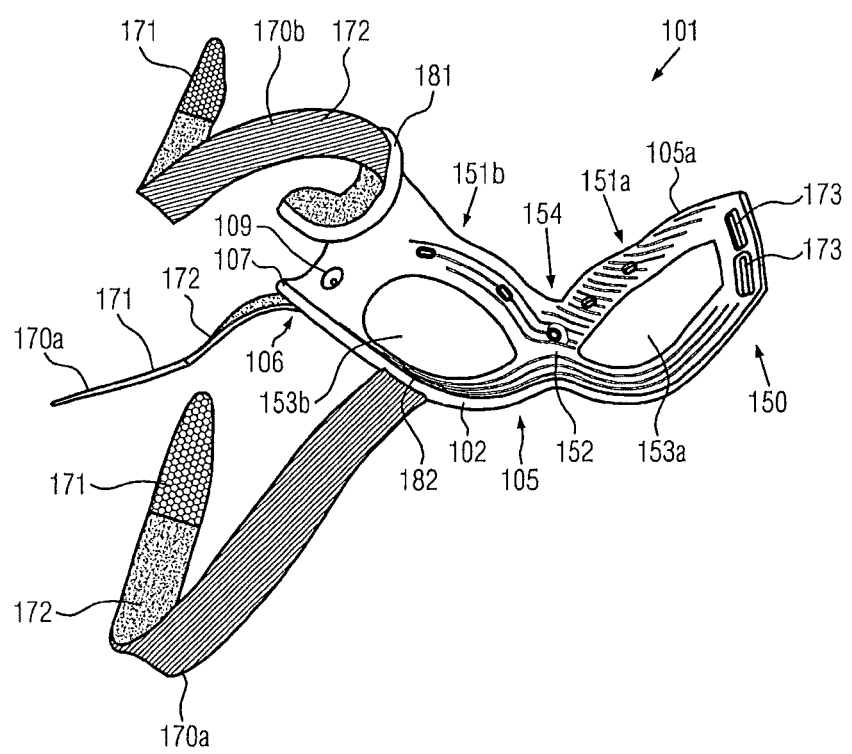
FIG. 18 shows a further perspective view of the third embodiment of the orthosis according to the invention.
Figure 19:
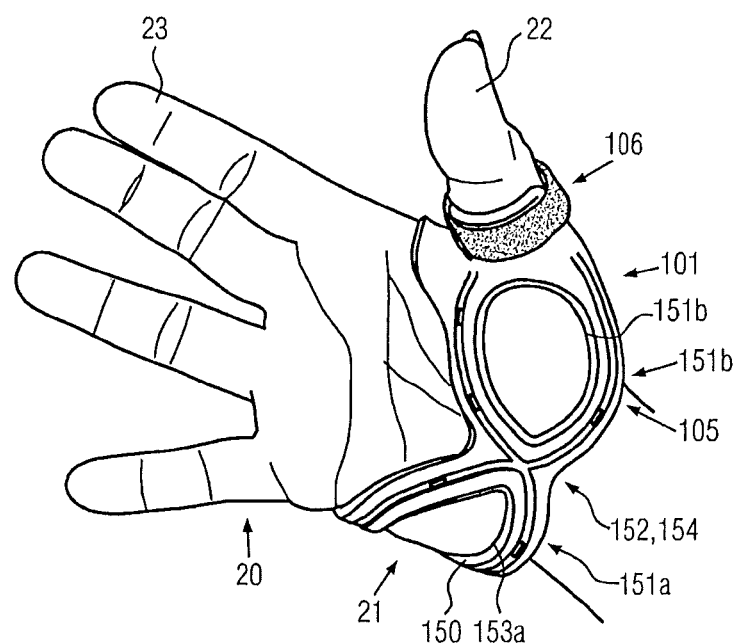
FIG. 19 shows a view of the palm of a hand with the orthosis according to the third embodiment placed thereon.
Figure 20:
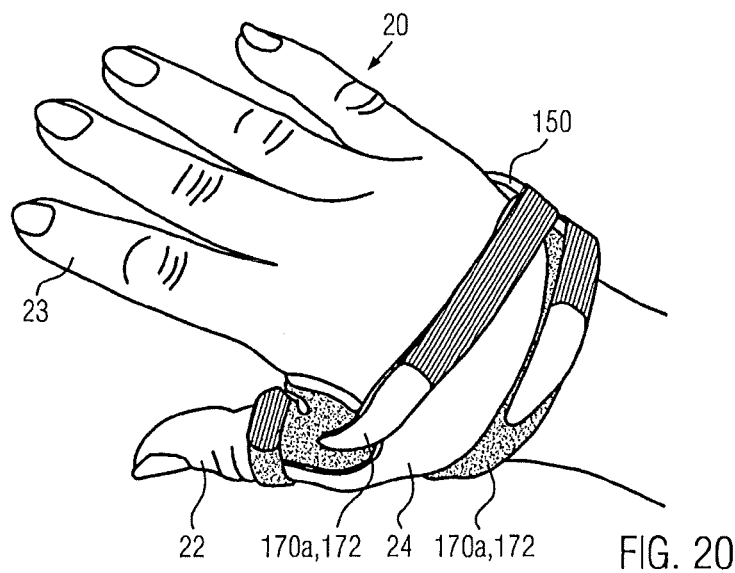
FIG. 20 shows a view of the back of the hand with the orthosis according to the third embodiment placed thereon.
Figure 21:
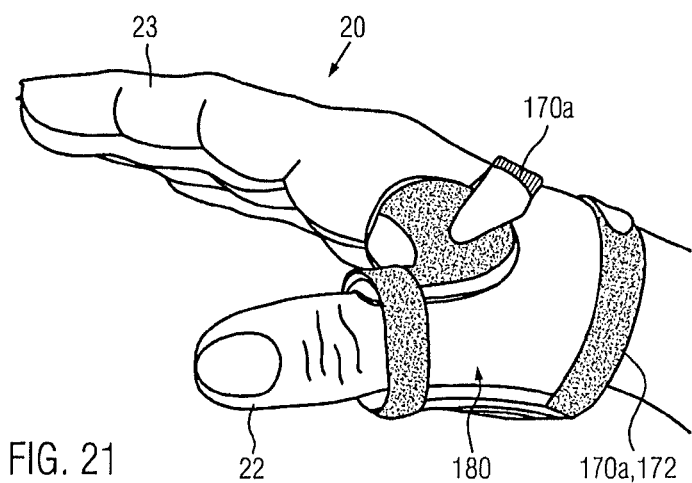
FIG. 21 shows a side view of the hand with the orthosis according to the third embodiment placed thereon.
Figure 22:
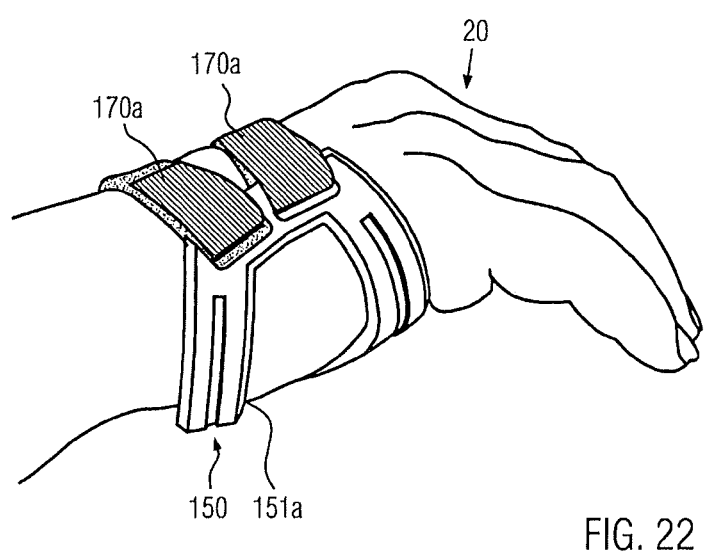
FIG. 22 shows a further side view of the hand with the orthosis according to the third embodiment placed thereon.

As is shown in FIG. 18, the orthosis 101 has two first touch and close bands 170a and a second touch and close band 170b as a closure device for fastening the orthosis 101 when placed on a hand. Each touch and close band 170a, 170b has a touch and close element 171 in an end region and a further touch and close element 172 at least along part of its remaining length, wherein the touch and close elements 171 and 172 can be fastened releasably to each other. The touch and close bands 170a, 170b are in each case permanently fastened at one end to the metacarpal section 105 or the thumb section 106. In the variant of FIGS. 15 to 17, the touch and close bands 170a, 170b (not illustrated there) are, in contrast, releasable in their entirety from the metacarpal section 105 and the thumb section 106 and can be fastened to the metacarpal section 105 and the thumb section 106, for example in the position shown in FIG. 18 and FIGS. 19 to 22, in order to secure the orthosis 101 to a hand.

FIGS. 19 to 22 show the orthosis 101 when placed onto a human hand 20. In order to ensure that the body 102 can rest along most of its length against the hand 20, said body can in turn be provided with a certain degree of elasticity.

The metacarpal section 105 extends in the region of the metacarpus 21 transversely over the palm of the hand 20, wherein its first end 105a is arranged in the vicinity of the outer edge of the hand, but spaced apart therefrom, and its second end 105b is arranged in the region of the carpometacarpal joint 24. Part of the petering-out ball of the thumb is arranged here in the region of the concave section 151b and the passage opening 153b, and the concave section 151a and the passage opening 153a receive a region in the vicinity of the outer edge of the hand. The recess located therebetween in the palm receives the curvature provided by the convex section 152. The metacarpal section 105 is therefore anatomically preshaped corresponding to the typical shape of a human metacarpus, but can preferably have a certain degree of elasticity and/or a certain plastic deformability in order to improve adaptation to different hands 20.

The flexible section 150 adjacent to the first end 105a runs around the outer edge of the hand and in contact therewith, and, on the other side, the thumb section 106 extends outward from the metacarpal section 105 substantially as an extension of the palm, and therefore the thumb section 106, and in particular the ring-segment-shaped thumb holding section 107, is aligned in such a manner that the thumb 22 of the hand 20 can be placed onto the thumb section 106 and can be arranged in the interior space 110 defined by the thumb holding section 107 and that the inner side of the thumb 22 can be placed here onto the supporting surface 109. Otherwise, the same considerations as for the thumb holding sections 7 and 57 of the orthoses 1 and 51 apply to the configuration of the ring-segment-shaped thumb holding section 107.

In order to secure the orthosis 101 on the hand 20, after the orthosis 101 has been placed onto the hand 20, each of the touch and close bands 170a is placed, starting from the fastening point thereof on the thumb section 106 or the metacarpal section 105 in the vicinity of the thumb section 106, over the back of the hand 20 and, by the end having the touch and close element 171, is guided through a respective, assigned opening 173 which is provided in that end region of the flexible section 150 which is remote from the metacarpal section 105. Each touch and close band 170a is subsequently guided back again in order to form a loop, and its touch and close element 171 is fastened to its touch and close element 172 in such a manner that the touch and close band 170a is tensioned. In this state, the touch and close bands 170a, the metacarpal section 105, the thumb section 106 and the flexible section 150 form an annularly closed structure which surrounds the hand 20 and secures the orthosis 101 on the hand 20. The fastening point of the one of the two touch and close bands 170a can be arranged, for example, on a region 181 of the thumb section 106 or of the metacarpal section 105 for contact between thumb 22 and index finger 23, and the fastening point of the other of the two touch and close bands 170a can be arranged, for example, in a region 182 of the metacarpal section 105 for contact in the region of the carpometacarpal joint 24.

In addition, in order to secure the orthosis 101 on the hand 20, the touch and close band 107b is placed, starting from its fastening point on the thumb holding section 107, over the intermediate space 180 caused by the ring-segment-shaped design of said thumb holding section, and then the touch and close element 171 is fastened to the touch and close element 172 such that the touch and close band 107b together with the thumb holding section 107 completely surrounds the thumb 22 annularly.

By means of the arrangement of the thumb section 106, and in particular of the thumb holding section 107, and the alignment of the supporting surface 109, a support of the thumb 22 with respect to a movement in the direction of the palm is again provided, inter alia. Nevertheless, the important pinch grip can be carried out.

The foregoing description provides embodiments of the invention by way of example only. It is envisioned that other embodiments may perform similar functions and/or achieve similar results. Any and all such equivalent embodiments and examples are within the spirit and scope of the present invention and are intended to be covered by the appended claims.

We claim:

1. An orthosis for fastening to a human hand for immobilizing a carpometacarpal joint and metacarpophalangeal joint of a thumb of the hand, comprising
 a stiff body having two directly connected round shaped portions that anatomically correspond to a heel of the hand in which each round shaped portion includes round openings for receiving portions of the heel of the hand therethrough, the two directly connected round shaped portions form a metacarpal section and a stiff thumb section,
 the metacarpal section
  has a first end and a second end, which are spaced apart from each other, and
  is designed in such a manner that said metacarpal section can be brought into engagement with the human hand such that the metacarpal section rests exclusively in the region of the palm of the hand below the metacarpophalangeal joints of an index finger, middle finger, ring finger and little finger such that it extends in a direction between two edges of the hand over the palm, and
 the stiff thumb section
  extends from the metacarpal section and has a first end, which is fastened to the metacarpal section or is formed by part of the metacarpal section, and a second end,
  in a region of its second end, has a ring-shaped or ring-segment-shaped thumb holding section and
  is designed in such a manner that when the metacarpal section is brought into engagement with the hand, the thumb section can be placed at the thumb of the hand such that the thumb is arranged in a ring opening defined by the thumb holding section, and the thumb holding section extends over at least part of the circumference of the thumb and at least partially surrounds the thumb, and
  supports the thumb against a movement in the direction of the palm in a position in which the thumb and the index finger of the hand are put opposite each other and the index finger can be moved toward the thumb into contact therewith and can be moved away from the thumb, wherein
   the metacarpal section is designed in such a manner that, when the orthosis is placed onto the human hand and the metacarpal section has been brought into engagement with the hand and the thumb section has been placed against the thumb of the hand such that the thumb is arranged in the ring opening defined by the thumb holding section and the thumb holding section extends over at least part of the circumference of the thumb and at least partially surrounds the thumb, said metacarpal section rests against the hand exclusively in the region of the palm, the metacarpal section has a first surface for contact with the palm and an opposite, second surface which, when the orthosis is put on, is directed away from the hand, wherein the first surface has two concave sections and a convex section arranged between the two concave sections, and
   which furthermore has a closure device for fastening the orthosis when placed on the hand, wherein the closure device has at least one first fastening section which is arranged and configured in such a manner that, when the orthosis is placed on, said fastening section can be arranged and secured on the metacarpal section or the thumb section in such a manner that said fastening section runs over the back of the hand and, together with the metacarpal section, forms at least part of an annularly closed section of the orthosis, which section surrounds the hand.

2. The orthosis as claimed in claim 1, in which the stiff body is formed from an element, and the thumb section is formed by a section of the element, wherein the thumb section extends from the second end of the metacarpal section, and the first end of the thumb section is fastened to the second end of the metacarpal section or is formed by said end.

3. The orthosis as claimed in claim 2, in which the element of the stiff body and/or the thumb section comprise metal and/or plastic.

4. The orthosis as claimed in claim 1, in which a stiffener is provided in the region of the second end of the metacarpal section and/or of the first end of the thumb section.

5. The orthosis as claimed in claim 1, in which at least a partial region of the stiff body is plastically deformable for individual adaptation to the hands of various users.

6. The orthosis as claimed in claim 1, in which the metacarpal section is dimensioned in such a manner that said metacarpal section extends over at least 30% of the circumference of the ring opening which is defined by the ring corresponding to the segment.

7. The orthosis as claimed in claim 1, in which the stiff body has a padding which is arranged in such a manner that, following fastening to the hand of a user, said padding comes into contact with the hand.

8. The orthosis as claimed in claim 1, in which the metacarpal section is configured in such a manner that
   its first and second end lie opposite each other on an elongate side of a ring opening which is defined by a ring corresponding to a segment, and when placed onto a hand, are arranged on the palm, and
   the thumb section bends down with respect to the course of the metacarpal section at the second end thereof and extends away from the metacarpal section.

9. The orthosis as claimed in claim 8, in which the thumb holding section is ring-segment-shaped and surrounds more than 50% of the circumference of the ring opening which is defined by the ring corresponding to the ring-segment-shaped thumb holding section.

10. The orthosis as claimed in claim 8, in which the metacarpal section extends in a first plane, and the ring-shaped or ring-segment-shaped thumb holding section extends in a second plane, wherein the first and second plane are tilted in relation to each other.

11. The orthosis as claimed claim 8, in which the metacarpal section has, in the vicinity of its first end, a curvature which protrudes inward into the ring opening which is defined by the ring corresponding to the segment.

12. The orthosis as claimed in claim 8, in which an elongate element has a greatest width at the first end of the metacarpal section and tapers in the direction of the second end of the thumb section.

13. The orthosis as claimed in claim 1, in which the thumb holding section is of ring-segment-shaped design.

14. The orthosis as claimed in claim 1, in which the closure device further has a second fastening section which is arranged and configured such that, when the orthosis is placed on, said second fastening section can be at least partially guided around the thumb in such a manner that said second fastening section annularly surrounds the thumb together with the thumb holding section.

15. The orthosis as claimed in claim 1, in which, in each of the two concave sections, a passage opening is formed in the first surface and through the metacarpal section.

16. The orthosis as claimed in claim 1, in which, in the region of the convex section, the metacarpal section has a tapered portion in a direction transversely to the direction between the first end and second end of the metacarpal section and along the first surface.

17. The orthosis as claimed in claim 1, in which the metacarpal section merges at its first end into a flexible section.

* * * * *